(12) United States Patent
Nunez et al.

(10) Patent No.: US 8,287,561 B2
(45) Date of Patent: Oct. 16, 2012

(54) BALLOON-TYPE ACTUATOR FOR SURGICAL APPLICATIONS

(75) Inventors: George Nunez, Miami, FL (US); Mohammed Ike Juman, Miami, FL (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1565 days.

(21) Appl. No.: 10/187,144

(22) Filed: Jun. 28, 2002

(65) Prior Publication Data

US 2004/0002726 A1    Jan. 1, 2004

(51) Int. Cl.
*A61M 29/00* (2006.01)
*A61B 17/04* (2006.01)

(52) U.S. Cl. ............. 606/191; 606/170; 227/180.1

(58) Field of Classification Search .......... 606/191–199; 600/207, 208; 264/464, 632, 512, 532, 563, 264/145; 604/103.11, 103.12, 103.13, 509, 604/32–34; 92/42–45; 30/180; 227/180.1
See application file for complete search history.

(56) References Cited

U.S. PATENT DOCUMENTS

| | | | | |
|---|---|---|---|---|
| 2,849,002 A * | 8/1958 | Oddo | | 606/192 |
| 3,727,614 A * | 4/1973 | Kniazuk | | 604/115 |
| 3,888,003 A * | 6/1975 | Brown | | 30/180 |
| 4,389,208 A * | 6/1983 | LeVeen et al. | | 604/95.03 |
| 4,447,227 A * | 5/1984 | Kotsanis | | 604/95.03 |
| 4,550,833 A * | 11/1985 | Hoheisel et al. | | 206/527 |
| 5,219,111 A | 6/1993 | Bilotti et al. | | |
| 5,288,290 A * | 2/1994 | Brody | | 604/32 |
| 5,634,883 A * | 6/1997 | Chin et al. | | 600/204 |
| 5,752,971 A * | 5/1998 | Rosenbluth et al. | | 606/192 |
| 5,893,866 A * | 4/1999 | Hermann et al. | | 606/192 |
| 6,015,382 A | 1/2000 | Zwart et al. | | |
| 6,099,518 A * | 8/2000 | Adams et al. | | 604/523 |
| 6,506,196 B1 * | 1/2003 | Laufer | | 606/142 |
| 6,648,842 B2 * | 11/2003 | Horkel | | 601/45 |
| 2002/0062136 A1 | 5/2002 | Hillstead et al. | | |
| 2003/0111507 A1 * | 6/2003 | Nunez | | 227/180.1 |

FOREIGN PATENT DOCUMENTS

| | | |
|---|---|---|
| JP | 54-76778 | 6/1979 |
| JP | 2-114952 | 4/1990 |
| WO | 00/69344 | 11/2000 |
| WO | WO 02/24085 * | 3/2002 |

* cited by examiner

*Primary Examiner* — Tuan V Nguyen
(74) *Attorney, Agent, or Firm* — Fay Kaplun & Marcin, LLP

(57) ABSTRACT

An actuator for surgical applications includes an inflation fluid conduit extending from a proximal end which, when the actuator is in an operative configuration, remains outside a patient's body, to a distal end and an inflatable member coupled to the distal end of the inflation fluid conduit so that, when inflation fluid is supplied to the inflatable member via the inflation fluid conduit, the inflatable member is expanded from a collapsed configuration to an expanded configuration, wherein, when in the collapsed configuration, the inflatable member includes a fold extending substantially transverse to a longitudinal axis thereof so that, when inflation fluid is supplied thereto, the inflatable member expands substantially along the longitudinal axis.

16 Claims, 5 Drawing Sheets

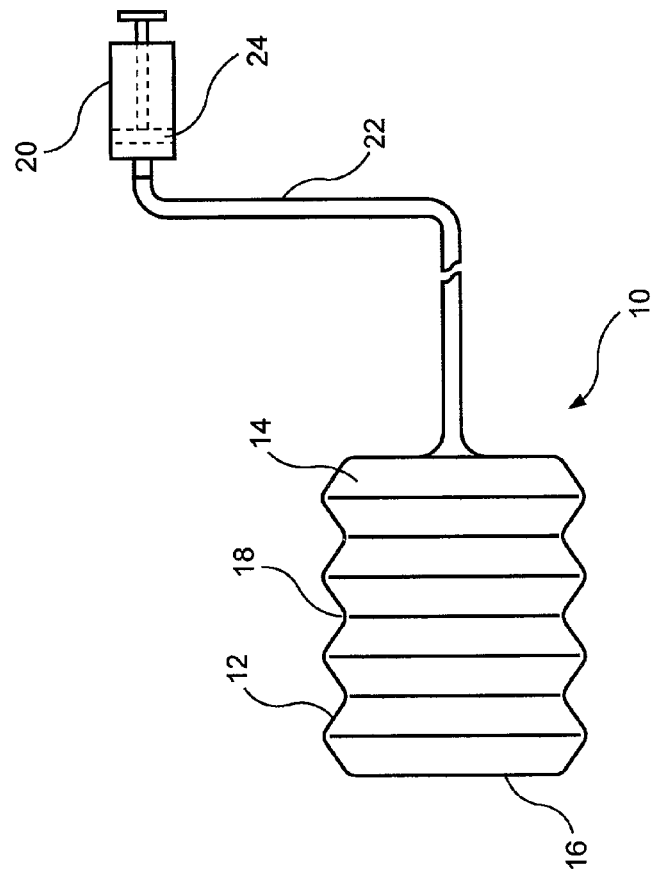
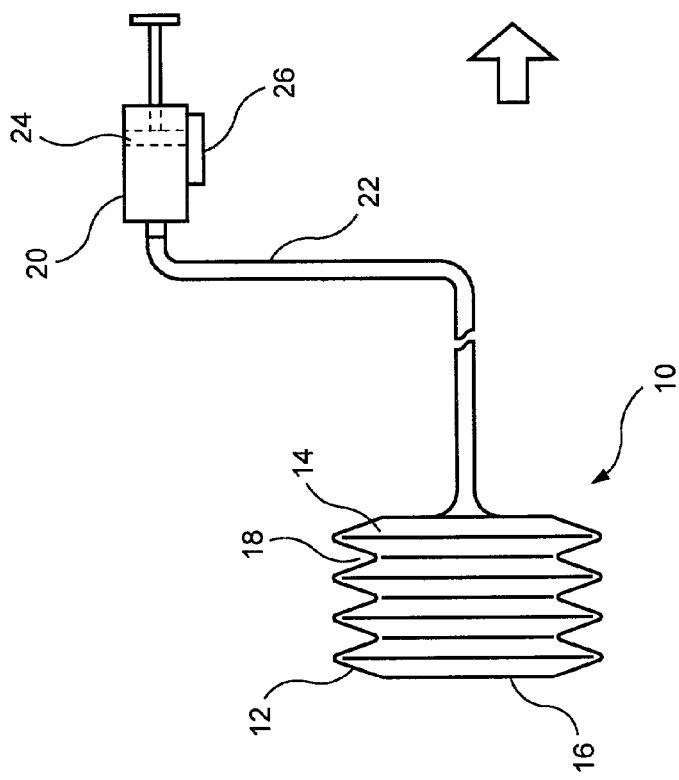

BALLOON-TYPE ACTUATOR FOR SURGICAL APPLICATIONS

FIELD OF THE INVENTION

Full thickness resection procedures involve excising a full thickness portion of an organ, approximating the surrounding tissue together to close up the hole created by the excision, and cutting away the excess tissue.

DESCRIPTION OF RELATED ART

Various conventional devices and procedures are available for resectioning lesions. However, activation of the various cutting, stapling and other functions of these devices requires actuators that are often bulky and/or which make the device excessively stiff.

Thus, many of these known resection devices and procedures have required at least one incision in an area near the portion of the organ to be excised to provide access to the lesion or treatment site.

The rigidity of conventional resectioning devices has been increased by the couplings which transmit the forces necessary to activate mechanisms included in the distal working heads thereof. A typical resectioning device of this type will include a proximal control handle coupled to a distal working head by a shaft with the working head operating on a portion of tissue to be treated. For example, it may be necessary to open and later close a gap between an anvil and a stapling head disposed in the working head while a portion of tissue to be excised is held in the gap. The staples must then be fired and a cutting blade must be activated to excise the tissue to be resected. The power to carry out these functions is generally transmitted from the control handle to the working head by one or more cables or drive shafts running the length of the shaft and increasing the stiffness of the device.

SUMMARY OF THE INVENTION

The present invention is directed to an actuator for use during surgery, comprising an inflation fluid conduit extending from a proximal end which, when the actuator is in an operative configuration, remains outside a patient's body, to a distal end in combination with an inflatable member coupled to the distal end of the inflation fluid conduit so that, when inflation fluid is supplied to the inflatable member via the inflation fluid conduit, the inflatable member is expanded from a collapsed configuration to an expanded configuration, wherein, when in the collapsed configuration, the inflatable member includes a fold extending substantially transverse to a longitudinal axis thereof so that, when inflation fluid is supplied thereto, the inflatable member expands substantially along the longitudinal axis.

BRIEF DESCRIPTION OF THE DRAWINGS

The accompanying drawings are included to provide a further understanding of the invention and are incorporated in and constitute part of the specification, illustrate several embodiments of the invention and, together with the description, serve to explain examples of the present invention. In the drawings:

FIGS. 1a, 1b are schematic side views of a balloon actuator for a surgical device according to the invention, shown in the deflated and inflated configurations;

DETAILED DESCRIPTION

Figure 2B:
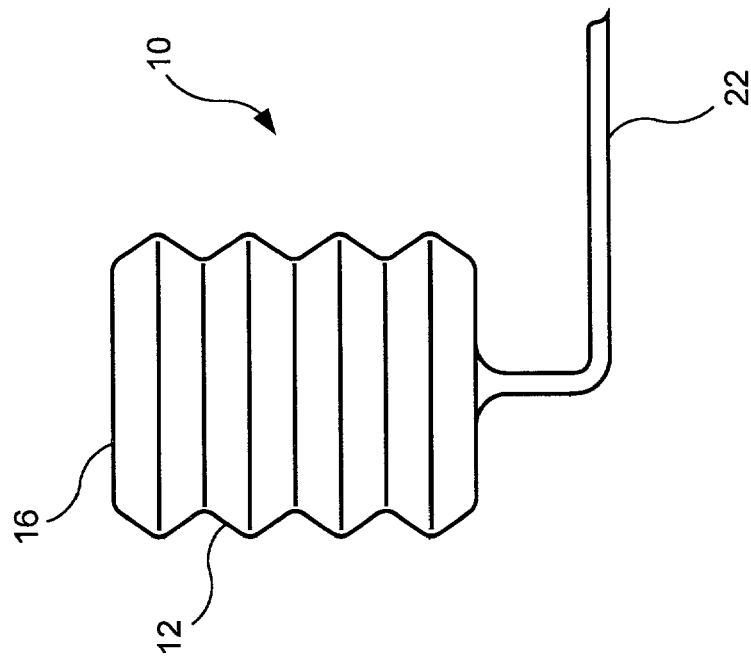
FIGS. 2a, 2b are schematic side views of a second embodiment according to the invention of a balloon actuator for a surgical device, shown in the deflated and inflated configurations.

The present invention is an actuator that may be used in surgical settings for actuating elements of surgical devices, or to directly displace structures or organs of the patient. As an example of the former usage, the actuator may as more fully described below, activate stapling and cutting functions of a full thickness resection device (FTRD). However, those skilled in the art will recognize that the actuator according to the present invention may be employed to activate any number of functions of a wide variety of devices for minimally invasive surgery, such as endoscopic and arthoscopic devices, etc.

FIG. 1 shows one exemplary embodiment of a balloon-type actuator 10 according to the present invention. Balloon actuator 10 includes an inflatable component 12 which, when deflated, is in a collapsed configuration shown in FIG. 1a, and, when inflated, is deployed in an expanded configuration shown in FIG. 1b. Inflatable component 12 may include an elastic shell 14 that expands when inflated. In one exemplary embodiment, the shell 14 is made of polyethylene or any other suitable material.

A force application surface 16 of the inflatable component 12 is intended to apply the force of expansion to an item to be repositioned—e.g., a component of a surgical instrument or an organ or selected portion of tissue. Force application surface 16 may, for example, be made of the same material as the shell 14, or of a less flexible material, so that force may be applied therefrom with less deformation of the inflatable component 12. In addition, surface 16 may be shaped to best apply the force of inflation for a particular application such as, by forming the inflatable component 12 so that, when in the expanded configuration, a shape of the surface 16 corresponds to a shape of the item to be repositioned.

Inflatable component 12 may be formed of a molded material, so that, when an inflating pressure is withdrawn therefrom, the inflatable component 12 naturally returns to the collapsed configuration. For example, accordion-like folds 18 may be formed in shell 14 such that they are biased to retract into the contracted position. That is, at any time that no inflation pressure is applied thereto, the bias of the accordion-like folds 18 causes them collapse onto one another to reduce a longitudinal length of the actuator 10 to the contracted position as shown in FIG. 1a. Folds 18 may be molded in the material of shell 14, or may be formed by separate resilient rings that apply a radial force to the inflated shell 14. Furthermore, as would be understood by those of skill in the art, the resilient characteristics of the inflatable component 12 may be selected to apply a force opposite in direction to the force applied by the supply of inflation pressure to the inflation of shell 14 to bias the actuator 10 into the contracted configuration.

For certain applications may be beneficial to control a direction of expansion of the inflatable component 12. For example, it may be useful in certain applications to expand the actuator 10 substantially entirely in one direction or to favor expansion in one direction, rather than expanding the inflatable component 12 symmetrically in all directions. This result may be achieved by the accordion-like design shown in FIGS. 1*a* and 1*b*, in which the majority of the expansion is substantially in the longitudinal direction. Those skilled in the art will understand that other approaches may be taken to achieve the same result. For example, the shell 14 of the inflatable component 12 may be formed of fibers that allow expansion in a desired direction but which substantially prevent expansion in directions perpendicular to the desired direction. For example, as would be understood by those of skill in the art, weaves of fibers such as Kevlar™ may be produced which are substantially rigid in a longitudinal direction while permitting a predetermined amount of expansion in a transverse direction.

Inflatable component 12 may be connected to an inflation device 20 via an inflation conduit 22. For example, inflation device 20 may be a hand operated pump with a piston 24, that allows the operator to control an inflation level of the actuator 10, and, consequently, the force being applied to the item to be repositioned. A scale 26 may be used to determine an amount of inflation of the inflatable component 12, when this cannot be directly observed.

Figure 2A:
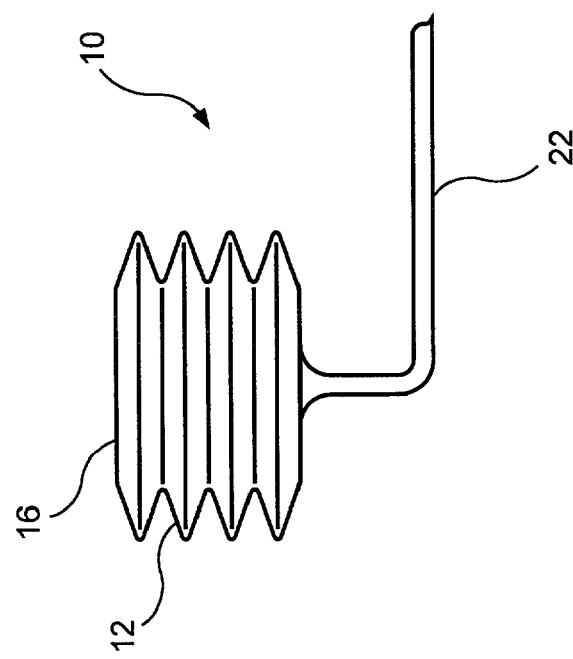

FIG. 2 shows an alternative embodiment of the invention, in which the actuator 10 includes an inflatable component 12 extending at an angle from the conduit 22. This configuration may be useful for applications in which the conduit 22 is stiff, or is coupled to a stiffening structure, for example to assist in propelling the inflatable component 12 through a body lumen. By angling the inflatable component 12 relative to the conduit 22, it is possible to use the actuator 10 to apply a force in a desired direction. As indicated before, the actuator 10 may be used to operate a component of a component of a surgical device, or may be used to directly reposition an organ or a portion of tissue. In the latter application, it may be necessary for conduit 22 to be rigid, to use the conduit 22 to apply force to the inflatable component 12 to obtain the necessary orientation thereof, and to maintain a desired position of the actuator 10 during inflation so that the desired force is applied at the proper location and in the desired direction. FIG. 2 shows an arrangement for achieving this by rotating the conduit 22 once the inflatable component 12 has been placed in the desired location.

Figure 3B:
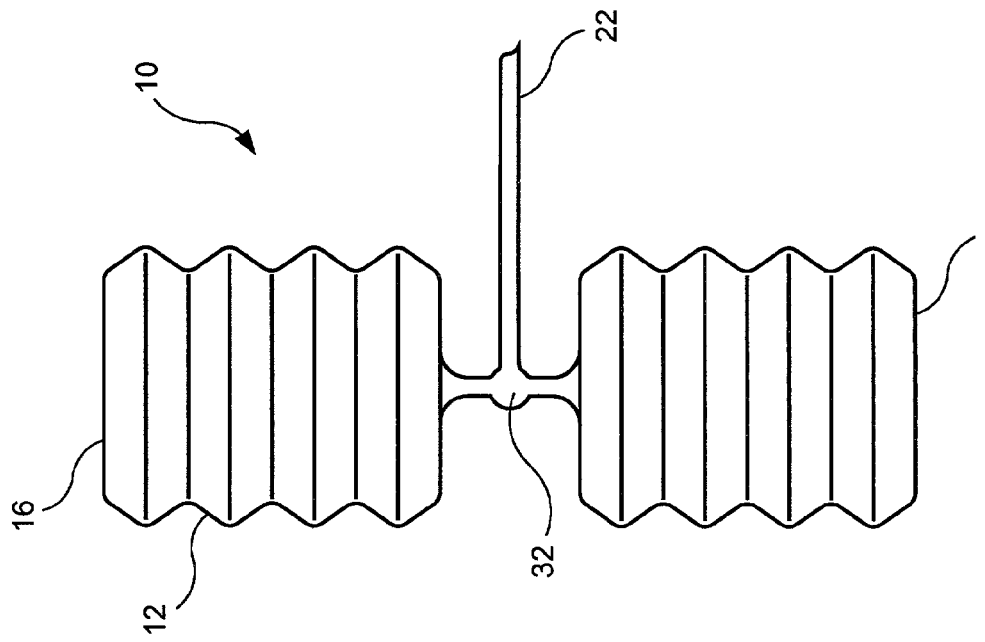
FIGS. 3a, 3b are schematic side views of a third embodiment of a balloon actuator for a surgical device, shown in the deflated and inflated configurations.
Figure 3A:
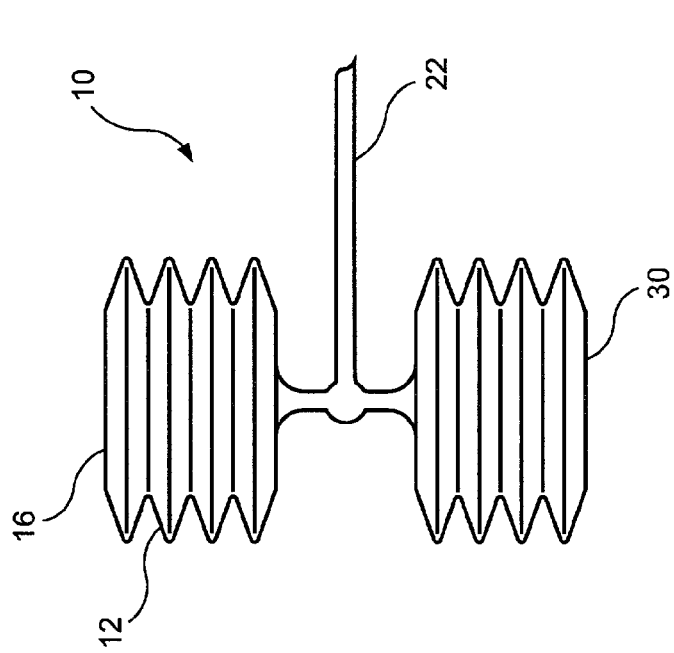

Additional configurations of actuator 10 may be devised using combinations of more than one inflatable component 12. As shown in FIG. 3, the actuator may include a first inflatable component 12 and a second inflatable component 12' that may also be inflated from a collapsed configuration as shown in FIG. 3*a* to an expanded configuration shown in FIG. 3*b*. The inflatable components 12, 12' may be inflated simultaneously using a single conduit 22, or may, alternatively, be inflated individually, using separate conduits or a control valve disposed, for example, at junction 32. Depending on the application, more than two inflatable components 12 may be used in actuator 10, to apply forces in the same or different directions.

Figure 4:
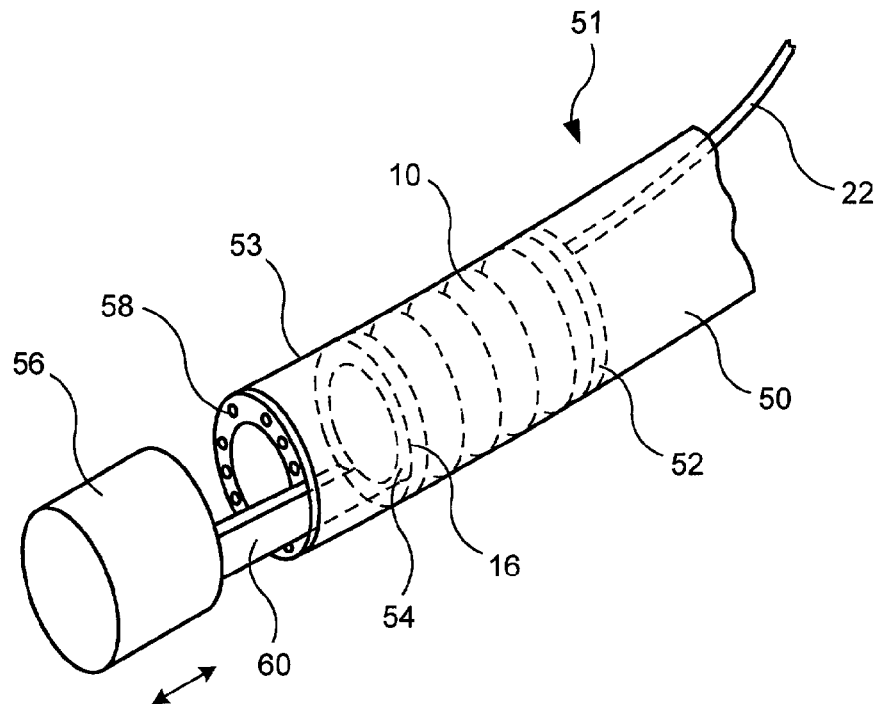
FIG. 4 is a perspective view of a balloon actuator used to move the anvil portion of an FTRD.

FIG. 4 shows an exemplary use of the actuator 10 within a full thickness resectioning device (FTRD) 51. FTRD 51 comprises a substantially flexible tube portion 50 that extends from a proximal part of the device, not shown, to a distal head portion 53 which, in an operative position, is inserted into a body lumen of the patient and advanced to a desired location therwithin. An anvil portion 56 is attached to the head portion 53 by a linkage 60, so that anvil portion 56 may be moved relative to head portion 53. In particular, the distance between anvil portion 56 and staple slots 58, formed on head portion 53, may be controlled by extending or retracting linkage 60. This allows the FTRD to be opened to draw body tissue in the head portion 53, and then be closed to a correct position in which the staples may be deployed from staple slots 58.

Actuator 10 is placed inside the FTRD 51, with inflation conduit 22 extending, for example, to the proximal end of the device along flexible tube portion 50. One end of the actuator 10 may be held stationary relative to the head portion 53 of the FTRD 51, for example by abutting a flange 52. This prevents the actuator 10 from moving out of position when a force is being applied thereto. Force application surface 16 of actuator 10 may be designed to interface with yoke 54, which is slidable within head portion 53 in the longitudinal direction. Yoke 54 is attached to anvil portion 56 by linkage 60, so that when yoke 54 moves, the anvil portion 56 is moved therewith.

When a pressurized fluid is provided to actuator 10 via conduit 22, the actuator inflates to the expanded configuration, pushes on the yoke 54, and causes the anvil portion 56 to move further from the staple slots 58. When the pressure is released, the actuator 10 deflates and preferably returns to the collapsed configuration. If the force application surface 16 is attached to yoke 54, the actuator 10 may move the yoke 54 to the original position as it collapses. This may be further facilitated by forming the actuator 10 so that it tends to return to the collapsed configuration when deflated, as explained above, or by using additional resilient members, separate from the actuator 10, to bias the anvil portion 56 to the closed position.

An analogous configuration may easily be devised where expansion of the actuator 10 closes the gap rather than opening it. For example, this may be done by reversing the position of the yoke 54 and flange 52 relative to the actuator 10.

Figure 5:
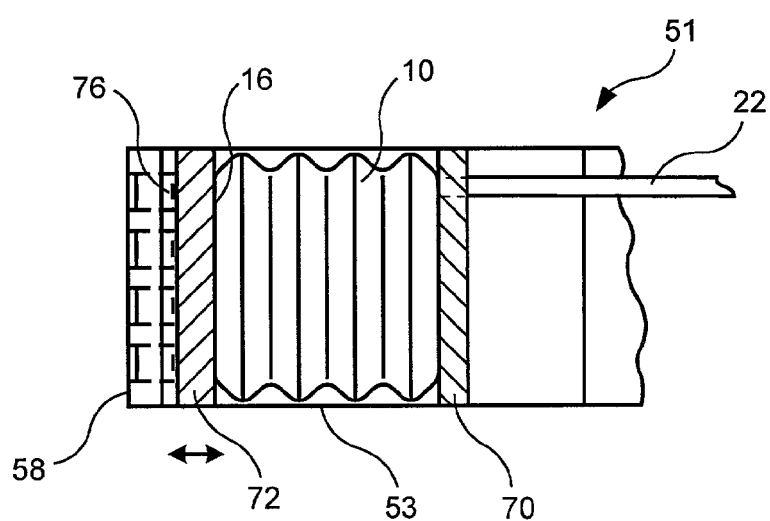
FIG. 5 is a cut-away side view of a balloon used to actuate the staples of an FTRD.

In another embodiment, the actuator 10 may be used to propel staples from the FTRD. As shown in FIG. 5, the actuator 10 may be placed in the head portion 53 of FTRD 51, so that it abuts a flange 70 that is fixed relative to the head portion 53. The force application surface 16 abuts a staple drive 72, which is slidably placed in head portion 53 so that it may translate longitudinally relative thereto. When the actuator 10 is inflated via the conduit 22, it pushes on the staple drive 72, which in turn forces the staples 76 out of the staple slots 58. In this manner, the staples 76 may be fired from the FTRD 51 without a mechanical linkage extending from a control handle to the head portion 53. Instead, only the a flexible conduit 22 extends from the control handle to the head portion 53. Those skilled in the art will understand that different known designs of staple drive 72 may be used with the actuator 10, such as rods pushing on individual staples, cam surfaces, or other force transmission members.

Figure 7:
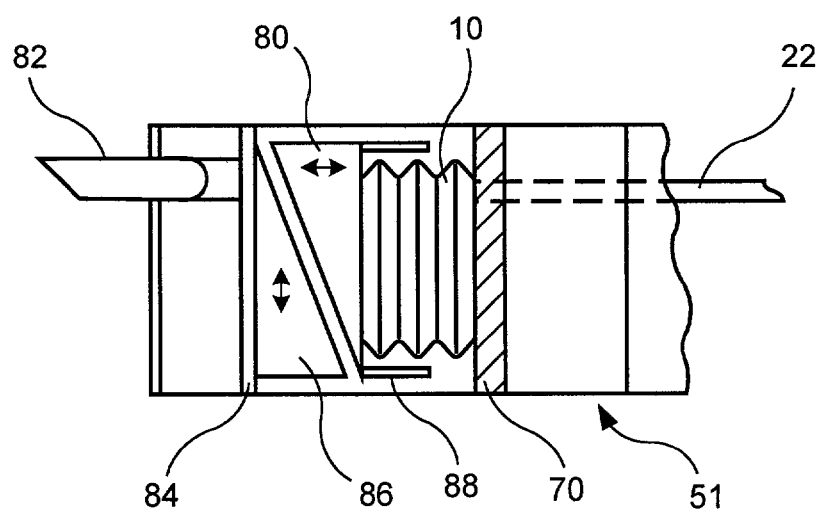
FIG. 7 is a cut-away side view of a balloon actuator used to actuate a blade of an FTRD.

FIG. 7 shows another embodiment of the invention where the actuator 10 operates a cam 80, which moves a blade 82 of the FTRD 51 along a track 84. The longitudinal force applied by the actuator 10 on the cam 80 causes a circumferential movement of the blade 82, for example due to the interaction of a wedge shaped cam 80 and a wedge shaped base 86 of the blade 82. Guides 84 may be used to control the movement of the base 86, while the guides 88 control the movement of the cam 80. Alternatively, the actuator 10 may be positioned to directly provide to the blade 82 a force along the circumferential direction.

Figure 6:
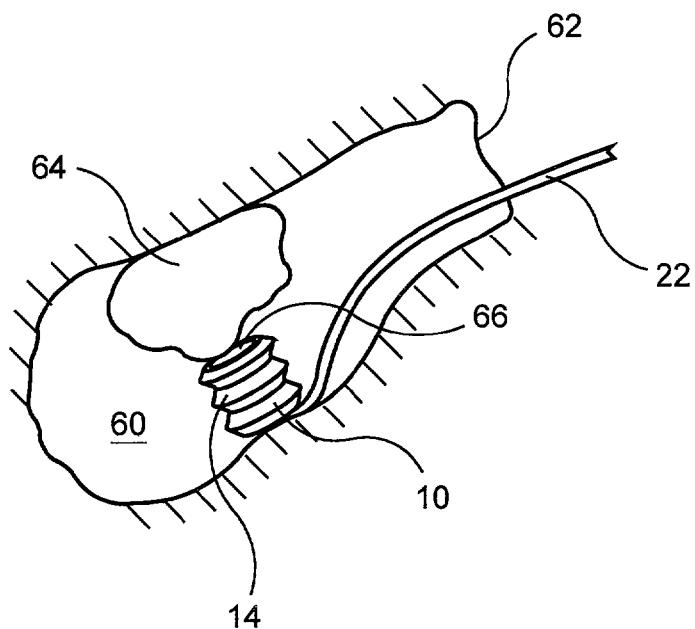
FIG. 6 is a cut-away side view of a balloon actuator used to move an organ or tissue.

A different application of the actuator 10 is described with reference to FIG. 6. In this embodiment, the actuator 10 is inserted into a patient's body via, for example, a body cavity 60, and is used to move an organ or portion of tissue 64 of the patient, for example, in an arthoscopic procedure where a separation is required between to structures. More specifically, an actuator 10 which may, for example, be substantially disc-shaped, and which includes an inflatable component 12 may be inserted between two vertebrae 64 which need to be separated from one another by a predetermined distance. The inflatable component 12 is attached to a source of inflation fluid via an axially reinforced conduit 22. The axial reinforcement of the conduit 22 allows an operator to position the inflatable component 12 between the vertebrae 64 by applying a force axially therealong. Alternatively, the actuator 10 may be deployed and manipulated into position between the vertebrae 64 using an arthoscope or similar device with the conduit 22 running through the arthoscope.

As would be understood by those of skill in the art, depending on how the particular tissue 64 has to be moved, an actuator 10 configured as shown in any of FIG. 1, 2, or 3 may be selected, or an actuator 10 having a different configuration providing the required movement of the organ or tissue 64 may be used. In addition, an organ or tissue contacting surface 66 may be provided, having a shape that facilitates repositioning of the particular organ or portion of tissue 64 to be moved, without damaging it.

It will be apparent to those of ordinary skill in the art that various modifications and variations may be made in the structure and the methodology of the present invention, without departing from the spirit or scope of the invention. Thus, it is intended that the present invention cover the modifications and variations of this invention provided they come within the scope of the appended claims and their equivalents.

What is claimed is:

1. An actuator for use during surgery, comprising:
    a first inflation fluid conduit extending from a proximal end which, when the actuator is in an operative configuration, remains outside a patient's body, to a distal end;
    a first inflatable member coupled to the distal end of the first inflation fluid conduit so that, when inflation fluid is supplied to the first inflatable member via the first inflation fluid conduit, the first inflatable member is expanded from a collapsed configuration to an expanded configuration, wherein, when in the collapsed configuration, the first inflatable member includes a plurality of folds extending substantially transverse to a longitudinal axis thereof so that, when inflation fluid is supplied thereto, the first inflatable member expands substantially along the longitudinal axis, wherein each of the plurality of folds includes a peak and a valley, the valley being disposed closer to the longitudinal axis than the peak, wherein the first inflatable member includes a force application surface for applying a force of expansion to a structure, the force application surface including a closed surface; and
    a plurality of resilient members, separate from the first inflatable member, arranged around a periphery of the first inflatable member, each of the plurality of resilient members disposed at a respective one of the valleys, and exerting a radial force for achieving the collapsed configuration.

2. The actuator according to claim 1, wherein the first inflatable member further comprises a resilient side surface biased to urge the first inflatable member toward the collapsed configuration.

3. The actuator according to claim 2, wherein the resilient side surface is a molded surface.

4. The actuator according to claim 1, wherein the longitudinal direction of the first inflatable member extends substantially in a direction from proximal to distal.

5. The actuator according to claim 1, wherein the longitudinal direction of the first inflatable member extends substantially perpendicular to an axis of the first inflation fluid conduit at the distal end of the first inflation fluid conduit.

6. The actuator according to claim 1, further comprising a second inflatable member selectively coupleable to a source of inflation fluid.

7. The actuator according to claim 1, further comprising a hand operated pump coupled to the proximal end of the first inflation fluid conduit.

8. The actuator according to claim 6, wherein the second inflatable component is coupled to the first inflation fluid conduit.

9. The actuator according to claim 6, wherein the second inflatable component is coupled to a distal end of a second inflation fluid conduit, the second inflation fluid conduit extending from a proximal end coupled to a source of inflation fluid.

10. The actuator according to claim 8, further comprising a control valve coupled to the first inflation fluid conduit for directing inflation fluid supplied thereto to a selected one of the first and second inflatable members.

11. The actuator according to claim 1, wherein the first inflatable member is constructed so that a profile thereof in a plane perpendicular to the longitudinal axis thereof remains substantially constant as the first inflatable member is expanded along the longitudinal axis.

12. A medical device comprising:
    a first inflation conduit extending from a proximal end which, when the medical device is in an operative configuration, remains outside a patient's body, to a distal end;
    a first inflatable member coupled to the distal end of the first inflation fluid conduit so that, when inflation fluid is supplied to the first inflatable member via the first inflation fluid conduit, the first inflatable member is expanded from a collapsed configuration to an expanded configuration, wherein, when in the collapsed configuration, the first inflatable member includes a plurality of folds extending substantially transverse to a longitudinal axis thereof so that, when inflation fluid is supplied thereto, the first inflatable member expands substantially along the longitudinal axis, wherein each of the plurality of folds includes a peak and a valley, the valley being disposed closer to the longitudinal axis than the peak;
    a plurality of resilient members, separate from the first inflatable member, arranged around a periphery of the first inflatable member, each of the plurality of resilient members disposed at a respective one of the valleys plurality of folds, and exerting a radial force for achieving the collapsed configuration; and
    an actuator of the medical device abutting a force application surface of the first inflatable member, expansion of the first inflatable member moving the actuator between an actuation position and a rest position, the force application surface being a closed surface.

13. The medical device according to claim 12, wherein the actuator comprises a cam operating a stapling mechanism.

14. The medical device according to claim 12, wherein the actuator comprises a cam operating a tissue cutting mechanism.

15. An actuator for use during surgery, comprising:
- a first inflation fluid conduit extending from a proximal end which, when the actuator is in an operative configuration, remains outside a patient's body, to a distal end;
- a first inflatable member coupled to the distal end of the first inflation fluid conduit so that, when inflation fluid is supplied to the first inflatable member via the first inflation fluid conduit, the first inflatable member is expanded from a collapsed configuration to an expanded configuration, wherein, when in the collapsed configuration, the first inflatable member includes a plurality of folds extending substantially transverse to a longitudinal axis thereof so that, when inflation fluid is supplied thereto, the first inflatable member expands substantially along the longitudinal axis, wherein each of the plurality of folds includes a peak and a valley, the valley being disposed closer to the longitudinal axis than the peak, wherein the first inflatable member includes a force application surface for applying a force of expansion to a structure, the force application surface including a closed surface shaped to correspond to a shape of the structure; and
- a plurality of resilient members, separate from the first inflatable member, arranged around a periphery of the first inflatable member, each of the plurality of resilient members disposed at a respective one of the valleys plurality of folds, and exerting a radial force for achieving the collapsed configuration.

16. A medical device comprising:
- a first inflation conduit extending from a proximal end which, when the medical device is in an operative configuration, remains outside a patient's body, to a distal end;
- a first inflatable member coupled to the distal end of the first inflation fluid conduit so that, when inflation fluid is supplied to the first inflatable member via the first inflation fluid conduit, the first inflatable member is expanded from a collapsed configuration to an expanded configuration, wherein, when in the collapsed configuration, the first inflatable member includes a plurality of folds extending substantially transverse to a longitudinal axis thereof so that, when inflation fluid is supplied thereto, the first inflatable member expands substantially along the longitudinal axis, wherein each of the plurality of folds includes a peak and a valley, the valley being disposed closer to the longitudinal axis than the peak;
- an actuator of the medical device abutting a force application surface of the first inflatable member, expansion of the first inflatable member moving the actuator between an actuation position and a rest position, the force application surface being a closed surface shaped to correspond to a shape of the actuator; and
- a plurality of resilient members, separate from the first inflatable member, arranged around a periphery of the first inflatable member, each of the plurality of resilient members disposed at a respective one of the valleys, and exerting a radial force for achieving the collapsed configuration.

* * * * *

UNITED STATES PATENT AND TRADEMARK OFFICE
CERTIFICATE OF CORRECTION

| | | |
|---|---|---|
| PATENT NO. | : 8,287,561 B2 | Page 1 of 1 |
| APPLICATION NO. | : 10/187144 | |
| DATED | : October 16, 2012 | |
| INVENTOR(S) | : Nunez et al. | |

It is certified that error appears in the above-identified patent and that said Letters Patent is hereby corrected as shown below:

Claim 15, Column 7, Line 31:

"plurality of folds" should be deleted

Signed and Sealed this
Twenty-second Day of January, 2013

David J. Kappos
*Director of the United States Patent and Trademark Office*